(12) United States Patent
Schweikert (10) Patent No.: US 7,827,656 B2
(45) Date of Patent: Nov. 9, 2010

(54) LUER CLIP

(75) Inventor: Timothy M. Schweikert, Levittown, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 12/494,573

(22) Filed: Jun. 30, 2009

(65) Prior Publication Data

US 2009/0264868 A1    Oct. 22, 2009

Related U.S. Application Data

(62) Division of application No. 10/966,896, filed on Oct. 15, 2004, now Pat. No. 7,614,123.

(51) Int. Cl.
*A61M 5/32* (2006.01)
*A44B 99/00* (2010.01)

(52) U.S. Cl. .......................... 24/522; 403/397; 604/905

(58) Field of Classification Search .................. 24/522, 24/529, 591.1; 59/88; 604/538, 533, 534, 604/905; 403/397

See application file for complete search history.

(56) References Cited

U.S. PATENT DOCUMENTS

| | | |
|---|---|---|
| 1,989,823 A | 2/1935 | Raabe |
| 2,410,546 A | 11/1946 | McCabe |
| 3,881,753 A | 5/1975 | Bochory |
| 4,224,937 A | 9/1980 | Gordon |
| 4,230,109 A | 10/1980 | Geiss |
| 4,333,505 A | 6/1982 | Jones et al. |
| 4,405,163 A | 9/1983 | Voges et al. |
| 4,473,369 A | 9/1984 | Lueders et al. |
| 4,673,161 A | 6/1987 | Flynn et al. |

(Continued)

FOREIGN PATENT DOCUMENTS

GB    2086466 A    5/1982

(Continued)

OTHER PUBLICATIONS

Intl. Preliminary Report on Patentability dated Apr. 18, 2006; PCT/US2004/034203 (5 pages).

(Continued)

*Primary Examiner*—Robert J Sandy
(74) *Attorney, Agent, or Firm*—Anton P. Ness; Fox Rothschild LLP (57) ABSTRACT

A clip (100) for retaining a first conduit (210) to a second conduit (230), the first conduit including a first connector (220) and the second conduit including a second connector (240). The first connector is releasably connected to the second connector. The clip (100) comprises a base portion (110) and a first clip portion (120) extending away from the base portion. The first clip portion (120) has a first opening (140) that is sized to frictionally retain the first connector (220). The clip further comprises a second clip portion (150) disposed on the base portion (110) away from the first clip portion (120). The second clip portion (150) includes a second opening (170) that is sized to frictionally retain the second connector (240). A method for securing a first conduit (210) to a second conduit (230) by attaching a clip (100) to the first conduit and the second conduit is also provided.

6 Claims, 5 Drawing Sheets

U.S. PATENT DOCUMENTS

| | | | |
|---|---|---|---|
| 4,735,615 A | 4/1988 | Uddo, Jr. et al. | |
| 4,773,874 A | 9/1988 | Kopeski, Jr. | |
| 4,820,288 A | 4/1989 | Isono | |
| 4,826,486 A | 5/1989 | Palsrok et al. | |
| 4,997,421 A | 3/1991 | Palsrok et al. | |
| 5,037,405 A | 8/1991 | Crosby | |
| 5,248,306 A | 9/1993 | Clark et al. | |
| 5,285,556 A | 2/1994 | Shorin et al. | |
| 5,437,648 A | 8/1995 | Graves et al. | |
| 5,957,894 A | 9/1999 | Kerwin et al. | |
| 6,076,424 A | 6/2000 | McMurtrey et al. | |
| 6,179,863 B1 | 1/2001 | Kensey et al. | |
| 6,375,231 B1 | 4/2002 | Picha et al. | |
| 2005/0034729 A1 | 2/2005 | Dombrowski | |

FOREIGN PATENT DOCUMENTS

| | | |
|---|---|---|
| JP | 61-055581 (UM) | 4/1986 |
| JP | 01-133936 (UM) | 9/1989 |
| JP | 03-039056 | 4/1991 |
| JP | 03-039056 (UM) | 4/1991 |
| JP | UM H03-39056 | 4/1991 |

OTHER PUBLICATIONS

Intl. Search Report and Written Opinion dated Jan. 4, 2006; PCT/US2004/034203 (7 pages).

Office Action dated May 26, 2009; JP Application No. 2006-535373 (8 pages) Translation (3 pages).

Supplemtary European Search Report, dated Feb. 17, 2010; EP 04795379.9 (3 pages).

Office Action dated Feb. 16, 2010, JP Application No. 2006-535373 (3 pages) (translation: 2 pages).

Examination Report dated Jul. 14, 2010; European Application No. 04795379.9 (7 pages).

LUER CLIP

CROSS REFERENCE TO RELATED APPLICATION

This application is a Divisional of U.S. patent application Ser. No. 10/966,896 filed Oct. 15, 2004, which claims the benefit of U.S. Provisional Patent Application 60/554,882 filed on Mar. 19, 2004 and U.S. Provisional Patent Application 60/511,871 filed on Oct. 16, 2003.

FIELD OF THE INVENTION

The present invention relates to catheters for the extracorporeal treatment of patients. Specifically, this invention relates to devices that are used to releasably secure a catheter to an extracorporeal treatment device, such as a hemodialysis machine.

BACKGROUND OF THE INVENTION

Catheters may be located in various venous locations and cavities throughout the body of a patient for introduction of fluids to a body or removal of fluids from the body. Such catheterization may be performed by using a single catheter having multiple lumens. A typical example of a multiple lumen catheter is a dual lumen catheter assembly in which one lumen introduces fluid and the other lumen removes fluid. An example of such a dual lumen catheter assembly is the SPLIT-CATH® catheter (trademark of Medical Components, Inc.). Alternatively, catheterization may be performed by using multiple single-lumen catheters, such as TESIO® catheters (trademark of Medical Components, Inc.).

Generally, to insert any catheter into a blood vessel, the vessel is identified by aspiration with a long hollow needle in accordance with the well known Seldinger technique. When blood enters a syringe attached to the needle, indicating that the vessel has been found, a thin guidewire is then introduced, typically through a syringe needle or other introducer device into the interior of the vessel. The introducer device is then removed, leaving the guidewire within the vessel. The guidewire projects beyond the surface of the skin. At this point, several options are available to a physician for catheter placement. The simplest is to pass a catheter into the vessel directly over the guidewire. The guidewire is then removed, leaving the catheter in position within the vessel. However, this technique is only possible in cases where the catheter (for example, a small diameter dual lumen catheter) is of a relatively small diameter, made of a stiff material, and not significantly larger than the guidewire. If the catheter to be inserted is significantly larger than the guidewire, a dilator device containing a sheath is passed over the guidewire to enlarge the opening in the vessel. The dilator is then removed along with the guidewire, leaving the sheath in place, and the catheter is then passed through the sheath into the vessel. The guidewire is then removed, leaving the catheter in position within the vessel.

Each catheter lumen is typically connected to a distal end of an extension tube via a hub. Each extension tube has a standard connector at its proximal end for connection to a medical device, such as a hemodialysis machine. Such connectors are commonly referred to as "luers". A luer is a standard fitting that accommodates the fluid connection of the lumen to an extracorporeal treatment device, such as the hemodialysis machine, as well as a cap or an inducer for medicaments. Generally, in the hemodialysis process, the catheter luer is connected to a mating luer that is in fluid communication with to the hemodialysis machine. While the process of connecting the luers together generally forms a secure connection, there is a possibility that the connection would become disengaged, leading to blood loss, contamination or the introduction of air embolisms into the blood stream. It would be beneficial to provide a device that releasably attaches to the connection and provides additional security for the luer connection and resistance to detachment of the extracorporeal treatment device.

BRIEF SUMMARY OF THE INVENTION

Briefly, the invention provides a clip for retaining a first conduit to a second conduit, where the first conduit includes a first connector and the second conduit includes a second connector and the first connector is releasably connected to the second connector to place the first and second conduits in fluid communication with each other. The clip comprises a base portion and a first clip portion extending away from the base portion, where the first clip portion has a first opening that is sized to frictionally retain the first connector. The clip further comprises a second clip portion disposed, on the base portion away from the first clip portion, where the second clip portion includes a second opening that is sized to frictionally retain the second connector.

The invention further provides a clip for retaining a first conduit to a second conduit, the first conduit including a first connector and the second conduit including a second connector. The clip comprises a base portion, a proximal portion and a distal portion. The proximal portion comprises a first proximal leg and a second proximal leg and the second proximal leg is attachable to the first conduit. The distal portion comprises a first distal leg and a second distal leg with the second distal leg being attachable to the second conduit. The base portion is adjustable by pressing toward each other the proximal and distal portions after they are clipped onto the first and second conduits respectively until the proximal and distal portions abut the first and second connectors respectively.

Further, the invention provides a method for securing a first conduit to a second conduit. The method comprises providing a first conduit having a first connector, a second conduit having a second connector and a clip. The clip comprises a base and a first end and a second end extending perpendicularly from the base. The method comprises attaching the first connector to the second connector. The method further comprises attaching the first end of the clip to one of the first connector and the second connector and attaching the second end of the clip to the other of the first connector and the second connector.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
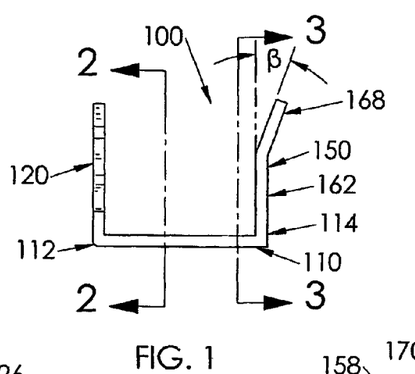
FIG. 1 is a side elevation view of a luer clip according to a first embodiment of the present invention.

In the drawings, like numerals indicate like elements throughout. Certain terminology is used herein for convenience only and is not to be taken as a limitation on the present invention. The words "proximal" and "distal" refer to the right side and the left side of the luer clip according to the present invention as shown in FIG. 1. Generally, in use, "proximal" refers to a direction that is closer to the extracorporeal treatment device or inserting physician and "distal" refers to a direction that is closer the patient or the inserted tip of the catheter. The terminology includes the words above specifically mentioned, derivatives thereof, and words of similar import. The following describes preferred embodiments of the invention. However, it should be understood based on this disclosure, that the invention is not limited by the embodiments described herein.

Referring now to the drawings in detail, there is shown in FIGS. 1-4 a luer clip 100 according to a first embodiment of the present invention. Preferably, the luer clip 100 is constructed from polypropylene or other plastic material and is relatively flexible, although those skilled in the art will recognize that the luer clip 100 may be constructed from other, suitable materials and be nondamaging to flexible medical tubing or their connectors.

The luer clip 100 includes a base 110 having a distal end 112 and a proximal end 114. The base 110 is generally parallelepiped in shape, with orthogonal sides. The base 110 is bisected by a plane 116 that extends perpendicularly from the plane of the paper in FIG. 4. The luer clip 100 is preferably a mirror image on either side of the plane 116.

Figure 2:
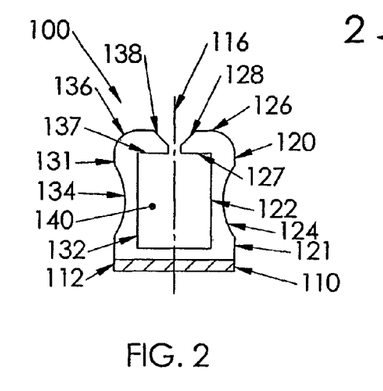
FIG. 2 is a sectional view of the luer clip taken along line 2-2 of FIG. 1.
Figure 3:
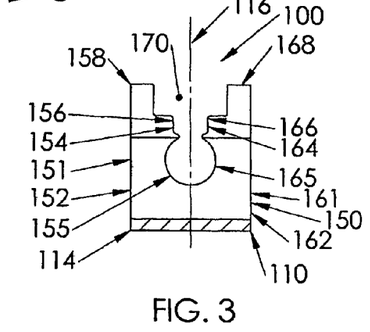
FIG. 3 is a sectional view of the luer clip taken along line 3-3 of FIG. 1.
Figure 4:
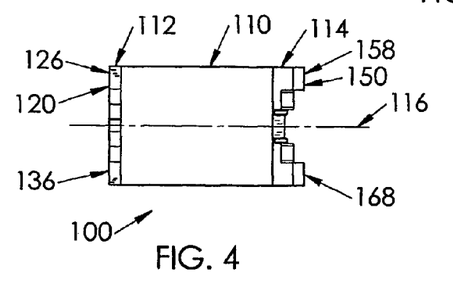
FIG. 4 is a top plan view of the luer clip of FIG. 1.

Referring to FIGS. 1 and 2, a distal clip portion 120 extends perpendicularly from the distal end 112. The distal clip portion 120 includes a first distal clip leg 121 having a generally flat interior side 122 and a generally concave exterior side 124. A tang 126 extends from a free end of the leg 121 toward the plane 116. The tang 126 includes a generally flat bottom face 127 and a beveled top face 128. The distal clip portion 120 also includes a second distal clip leg 131 having a generally flat interior side 132 and a generally concave exterior side 134. A tang 136 extends from a free end of the leg 131 toward the plane 116. The tang 136 includes a generally flat bottom face 137 and a beveled top face 138. The beveled top faces 128, 138 of tangs 126, 136 together define an outwardly widened and inwardly narrowed entrance to the clip opening 140. The first distal clip leg 121 and the second distal clip leg 131 are preferably mirror images of each other across the plane 116. The first distal clip leg 121 and the second distal clip leg 131 are separated by a generally rectangular opening 140 generally defined by the interior sides 122, 132, the bottom faces 127, 137, and the base 110. While a rectangular opening is shown in FIG. 2, those skilled in the art will recognize that the opening may be varied in shape. As shown in FIGS. 2 to 4, the base 110 is unslotted adjacent to the distal and proximal clip portions 120, 150 which are also unslotted adjacent to the base.

Referring now to FIGS. 1 and 3, a proximal clip portion 150 extends generally perpendicularly from the proximal end 114 of the base 110 and parallel to the distal clip portion 120. The proximal clip portion 150 includes a first proximal clip leg 151 having a generally flat exterior side 152 and an interior side 154. A lower portion 155 of the interior side 154 is arcuate, while an upper portion 156 of the interior side 154 is indented. An extension 158 extends at an angle β from the leg 151 away from the base 110 and the distal clip portion 120. Preferably, the angle β is approximately 30 degrees, although those skilled in the art will recognize that the angle β may be more or less than 30 degrees.

The proximal clip portion 150 also includes a second proximal clip leg 161 having a generally flat exterior side 162 and an interior side 164. A lower portion 165 of the interior side 164 is arcuate, while an upper portion 166 of the interior side 164 is indented. The lower portion 165 of the interior side 164 mates with the lower portion 155 of the interior side 154 to form an arc extending approximately 240 degrees. An extension 168 extends at an angle β from the leg 161 away from the base 110. Preferably, the angle β is approximately 30 degrees, although those skilled in the art will recognize that the angle β may be more or less than 30 degrees. The first proximal clip leg 151 and the second proximal clip leg 161 are separated by a generally U-shaped opening 170 generally defined by the interior sides 154, 164, with the lower portions 155, 165 of the interior sides 154, 164, respectively, forming the bottom portion of the "U". The generally U-shaped opening 170 and the indented upper portions 156, 166 of interior sides 154, 164 together define an outwardly widened and inwardly narrowed entrance to the clip opening at lower portions 155, 165 of the interior sides 154, 164 of first and second clip legs 151, 161.

Now with reference to FIGS. 5, 6, 6A and 7, a catheter assembly 200, to which the luer clip 100 is attached, is connected to a hemodialysis machine according to standard procedures. The hemodialysis machine includes an extracorporeal bloodline 230 with a male luer 240 (FIG. 6A) disposed on the distal end of the bloodline 230, shown in FIG. 5, that is releasably connected to the female luer 220 of the catheter assembly 200 according to known methods. The bloodline 230 includes a narrowed neck portion 232 disposed immediately proximate of the male luer 240.

Figure 6:
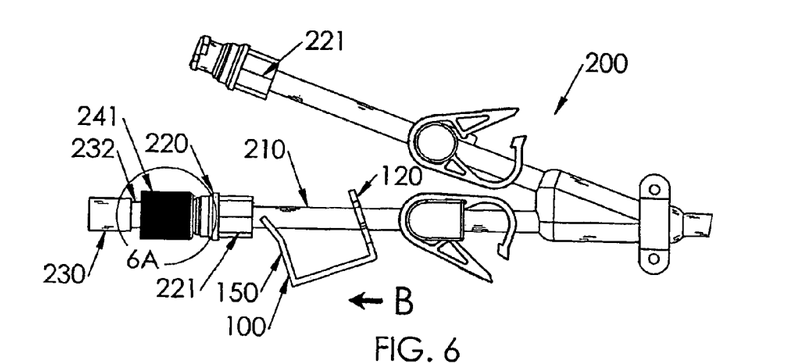
FIG. 6 is a side elevation view of the luer clip of FIGS. 1-4 being proximally translated along the extension tube of the catheter.
Figure 6A:
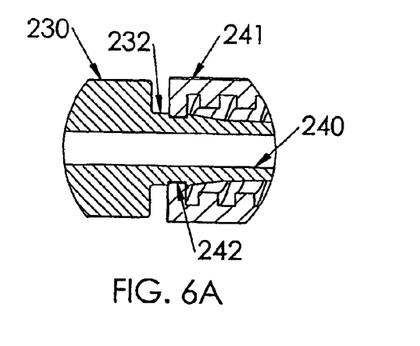
FIG. 6A is a sectional view of a portion of the luer clip shown in FIG. 6.

Preferably, as shown in FIGS. 6 and 6A, a retaining ridge 242 is disposed circumferentially around the male luer 240. A threaded swivel 241 is adapted to be snapped on to the male luer 240 and retained about the retaining ridge 242. As assembled, the threaded swivel 241 is free to rotate about the male luer, thereby facilitating a threaded engagement between the male luer 240 and the female luer 220 without having to rotate the male luer 240 or the female luer 220.

Figure 5:
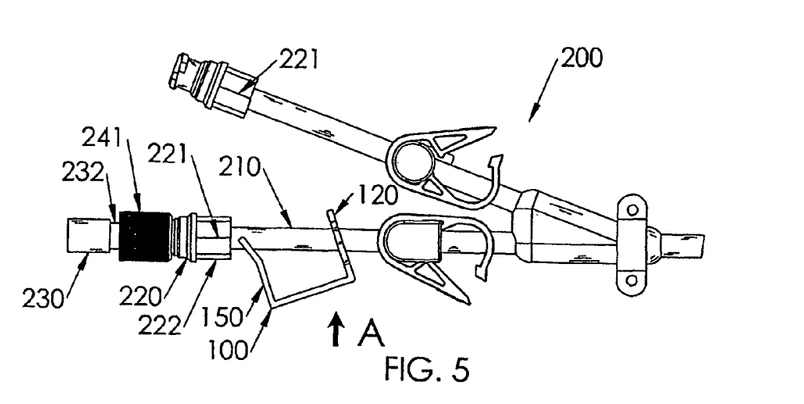
FIG. 5 is a side elevation view of the luer clip of FIGS. 1-4 being connected to an extension tube of a catheter.
Figure 7:
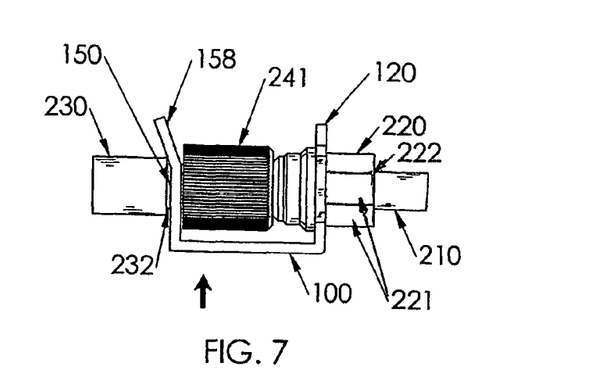
FIG. 7 is an enlarged side elevation view of the luer clip of FIGS. 1-4 connecting a female luer connector on a catheter to a male luer connector on a hemodialysis machine.

Referring now to FIG. 5, the clip 100 is connected to the catheter assembly 200 having an extension tube 210 with a female luer 220, having a distal end 222, disposed on the proximal end of the extension tube 210. At least one flat 221 is disposed on the distal end 222 of the female luer 220. Preferably, two flats 221 are located on opposing sides of the female luer 220. The flats 221 are disposed proximate to the interior sides 122, 132 of the distal clip portion 120 when the luer clip 100 is disposed about the female luer 220. While generally rectangular flats 221 are shown in FIGS. 5, 6 and 7, it will be known to those skilled in the art that the flats 221 may take any shape that will accommodate the profile of the rectangular opening 140 of the distal clip portion 120 as shown in FIG. 2. The clip 100 is connected to the catheter assembly 200 by disposing the catheter extension tube 210 into the generally rectangular opening 140 formed by the distal clip legs 121, 131 of the distal clip portion 120 and the base 110. During insertion, the extension tube 210 is forced against each of the beveled top faces 128, 138 of the tangs 126, 136, respectively. The tangs 126, 136 each are biased away from the plane 116, causing the legs 121, 131 to be deflectable laterally apart, sufficiently to allow the extension tube 210 to be urged past them to be disposed within the generally rectangular opening 140, as shown by the arrow "A". After the extension tube 210 is disposed within the generally rectangular opening 140, the resiliency of the material forming the luer clip 100 allows the tangs 126, 136 to return to their unbiased position, securely retaining the extension tube 210 within the generally rectangular opening 140.

The luer clip 100 is translated proximally along the extension tube 210, as shown by the arrow "B" in FIG. 6, until the distal end 222 of the female luer 220 on the proximal end of the extension tube 210 is disposed within the generally rectangular opening 140. The narrowed neck 232 of the bloodline 230 is then disposed within the generally U-shaped opening 170 until the bloodline 230 is urged past upper portions 156, 166 and engages the lower portions 155, 165 of the interior sides 154, 164 of the proximal clip legs 151, 161.

The narrowed neck portion 232 of the bloodline 230 is sufficiently long to frictionally retain the proximal clip portion 150 on the narrowed neck portion 232 between the bloodline 230 and the male luer 240. The proximal clip portion 150 is spaced from the distal clip portion 120 sufficiently to retain the female luer 220 and the male luer 240 therebetween. The clip 100 is now securely connected to the catheter assembly 200 and the bloodline 230, as shown in FIG. 7, so that the catheter assembly 200 and the bloodline 230 are securely connected to each other. Hemodialysis may now begin.

To remove the clip 100 from the bloodline 230 so that the bloodline 230 can be removed from the catheter assembly 200, the extensions 158, 168 are biased to the left and downward from the position shown in FIG. 7. The narrowed neck portion 232 of the bloodline 230 snaps out of the proximal clip portion 150 so that the clip 100 may be slid distally along the catheter extension tube 210. At this point, the hemodialysis machine and the catheter assembly 200 remain secured according to standard procedures, and the female luer 220 may be disconnected from the male luer 240 and the bloodline 230 is disconnected from the catheter assembly 200.

While only one extension tube 210 on the catheter assembly 200 is discussed, those skilled in the art will recognize that, for a multi-lumen catheter assembly, such as the catheter assembly 200 shown in FIGS. 5 and 6, a luer clip 100 may also be disposed on the remaining extension tube in the same manner as described above with respect to the extension tube 210.

Figure 8:
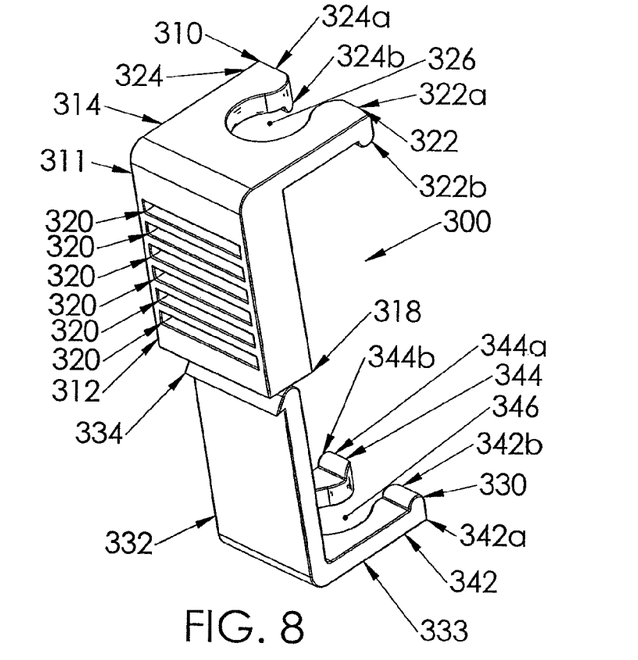
FIG. 8 is an exploded perspective view of a luer clip according to a second embodiment of the present invention.
Figure 9:
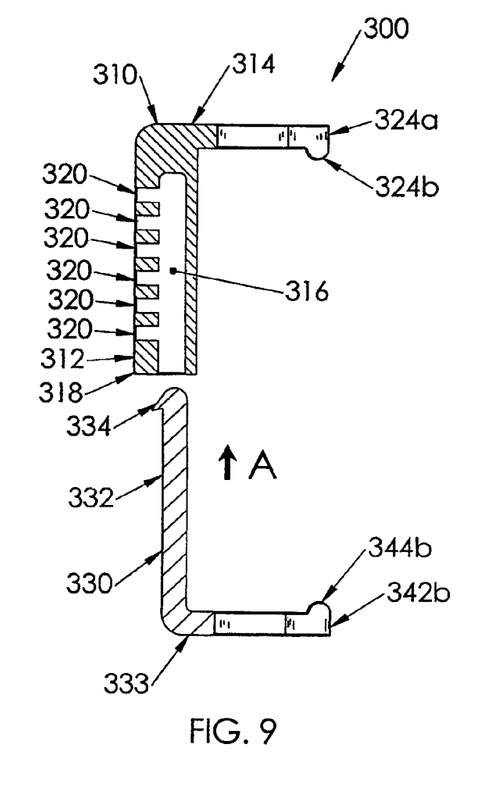
FIG. 9 is an exploded sectional view of the luer clip shown in FIG. 8.
Figure 10:
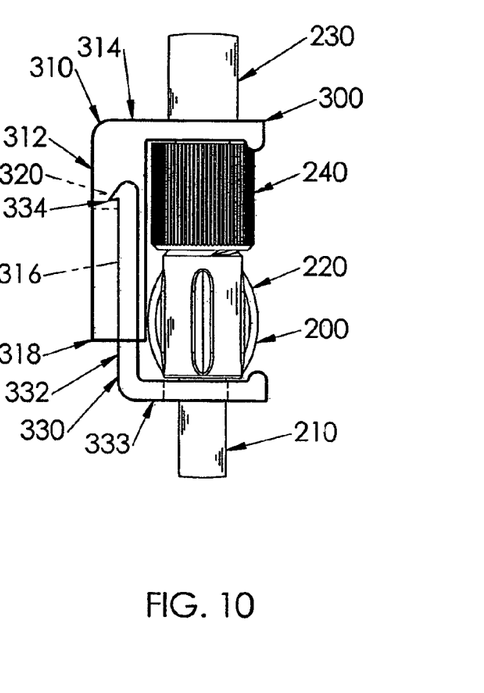
FIG. 10 is a side elevational view of the luer clip shown in FIGS. 8 and 9 being connected to a luer connection.

Referring now to FIGS. 8-10, a second embodiment of a luer clip 300 is shown. The luer clip 300 includes a proximal portion 310 and a distal portion 330. The proximal portion 310 is preferably generally "L-shaped", with a first leg 312 extending toward the distal portion 330 and a second leg 314 extending preferably perpendicular to the first leg 312. Preferably, the second leg 314 extends from a proximal end 311 of the proximal portion 310. The first leg 312 includes an insertion slot 316 (FIG. 9) that extends from a distal end 318 of the first leg 312 toward the second leg 314. Further, a plurality of locking slots 320 extend from the insertion slot 316 to the exterior of the first leg 312.

Figure 8A:
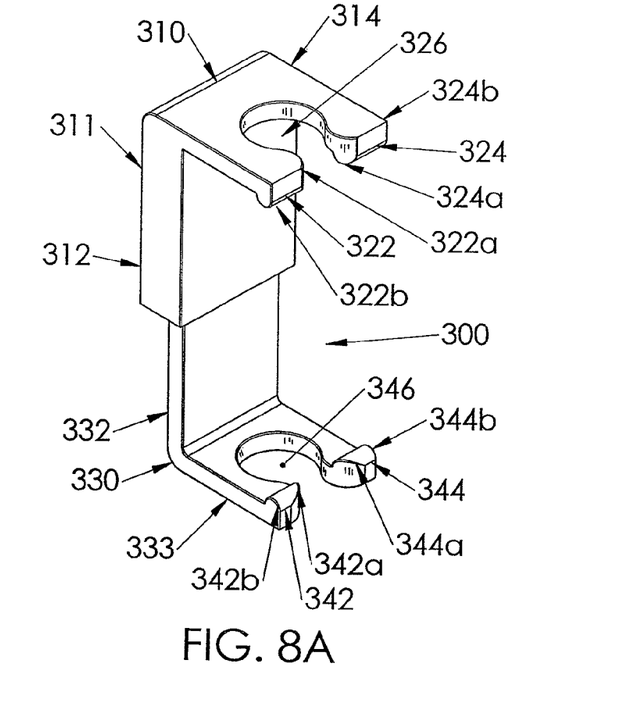
FIG. 8a is an alternate exploded perspective view of the luer clip of FIG. 8.

The second leg 314 includes a pair of preferably mirror image leg portions 322, 324. The leg portions 322, 324 are separated by a generally U-shaped opening 326. Free ends 322a, 324a of each of the leg portions 322, 324, respectively, extend into the generally U-shaped opening 326. Each free end 322a, 324a also includes a nub 322b, 324b that extends away from each leg portion 322, 324 generally toward the distal portion 330.

The distal portion 330 is preferably generally "L-shaped", with a first leg 332 extending toward the proximal portion 310 and a second leg 333 extending preferably perpendicular to the first leg 332, distal from the proximal portion 310. The first leg 332 is sized to be disposed within the insertion slot 316, and, together, first leg 312 of proximal portion 310 and first leg 332 of distal portion 330 define a base portion of the luer clip 300. The first distal leg 332 includes a locking section and the first proximal leg includes complementary locking elements arrayed along the insertion slot: the first leg 332 includes a beveled tab 334 that is sized to be disposed within any of the locking slots 320 when the first leg 332 is disposed within the insertion slot 316, such that first leg 312 and first leg 332 are adjustably positionable. During insertion, the first leg 332 of the distal portion 330 is slid towards the first leg 312 of the proximal portion 310, in the direction of the arrow "A" shown in FIG. 9.

The second leg 333 includes a pair of preferably mirror image leg portions 342, 344. The leg portions 342, 344 are separated by a generally U-shaped opening 346. Free ends 342a, 344a of each of the leg portions 342, 344, respectively, extend into the generally U-shaped opening 346. Each free end 342a, 344a also includes a nub 342b, 344b that extends away from each leg portion 342, 344 generally toward the proximal portion 310.

Referring now to FIG. 10, the catheter assembly 200 is connected to the extracorporeal bloodline 230, with the female luer 220 of the catheter assembly 200 releasably connected to the male luer 240 of the extracorporeal bloodline 230.

Preferably, the extracorporeal bloodline 230 is inserted between the leg portions 322, 324 of the proximal portion 310 and into the generally U-shaped opening 326 such that the first leg 312 is disposed toward the distal portion 330. Similarly, the extension tube 210 is inserted between the leg portions 342, 344 of the distal portion 330 and into the generally U-shaped opening 346 such that the first leg 332 is disposed toward the proximal portion 310. The first leg 332 of the distal portion 330 is then inserted into the insertion slot 316 and the proximal portion 310 and the distal portion 330 are drawn toward each other, with the distal portion 330 being slid in the direction of arrow "A" shown in FIG. 9, while securing the female luer 220 of the catheter assembly 200 and the male luer 240 of the extracorporeal bloodline 230 between the second leg 314 of the proximal portion 310 and the second leg 333 of the distal portion 330. The tab 334 engages one of the locking slots 320, securely retaining the distal portion 330 and the proximal portion 310 together. The clip 300 now securely connects the catheter assembly 200 and the extracorporeal bloodline 230.

The clip 300 may be removed in one of several ways. The clip 300 may be snapped apart, so that the clip 300 may not be reused. In such an instance, it is preferred that the clip 300 is constructed from a relatively brittle material, such as ABS or other suitable material. Alternatively, the clip 300 may be removed by forcing the tab 334 away from the locking slots 320 and pulling the proximal portion 310 and the distal portion 330 away from each other. In such an instance, it is preferred that the clip 300 is constructed from polyethylene, polypropylene, or some other suitable material.

Another alternate embodiment of a luer clip 400 according to the present invention is shown in FIGS. 11-14. The luer clip 400 includes a proximal portion 410 and a distal portion 430. The proximal portion 410 is preferably generally "L-shaped", with a first leg 412 extending toward the distal portion 430 and a second leg 414 extending preferably perpendicular to the first leg 412, distal from the distal portion 430. The first leg 412 includes an insertion slot 416 that extends from a distal end 418 of the first leg 412 toward the second leg 414. Further, a plurality of ratchet teeth 420 are disposed along the interior of the insertion slot 416. A first and a second retaining leg 419a, 419b are disposed on the first leg 410. Preferably the first and second retaining legs 419a, 419b are disposed on the side of the first leg 410 that is closer to the catheter assembly 200 when the luer clip 400 is disposed about the catheter assembly 200. The first retaining leg 419a is spaced apart from the second retaining leg 419b defining a channel 419c therebetween.

Figure 11:
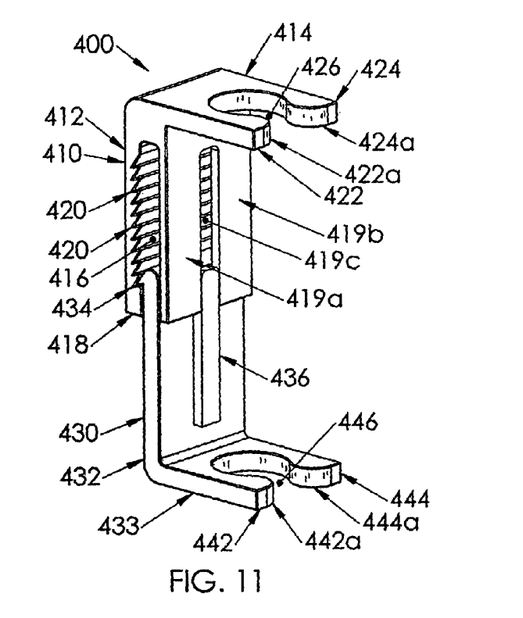
FIG. 11 is a perspective view of a luer clip according to a third embodiment of the present invention.
Figure 12:
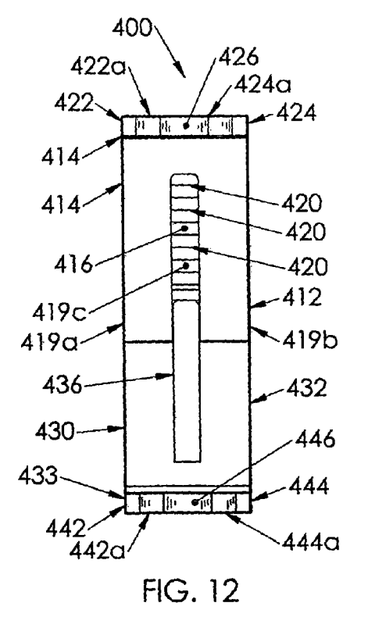
FIG. 12 is a front elevational view of the luer clip of FIG. 11.
Figure 13:
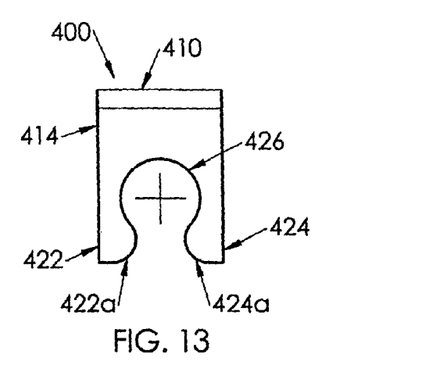
FIG. 13 is a top plan view of the luer clip of FIG. 12.

The second leg 414 includes a pair of preferably mirror image leg portions 422, 424. The leg portions 422, 424 are separated by a generally U-shaped opening 426. Free ends 422a, 424a of each of the leg portions 422, 424, respectively, extend into the generally U-shaped opening 426, forming a narrowed entrance for the opening.

The distal portion 430 is preferably generally "L-shaped", with a first leg 432 extending toward the proximal portion 410 and a second leg 433 extending preferably perpendicular to the first leg 432, distal from the proximal portion 410. The first leg 432 is sized to be disposed within the insertion slot 416. The first leg 432 includes a locking pawl 434 that is sized to engage the ratchet teeth 420 when the first leg 432 is disposed within the insertion slot 416. The first leg 432 also includes a reinforcing rib 436 juxtaposed away from the locking pawl 434 to provide support for the first leg 432. The reinforcing rib 436 is sized to fit into the channel 419c between the first retaining leg 419a and the second retaining leg 419b.

The second leg 433 includes a pair of preferably mirror image leg portions 442, 444. The leg portions 442, 444 are separated by a generally U-shaped opening 446. Free ends 442a, 444a of each of the leg portions 442, 444, respectively, extend into the generally U-shaped opening 446.

Figure 14:
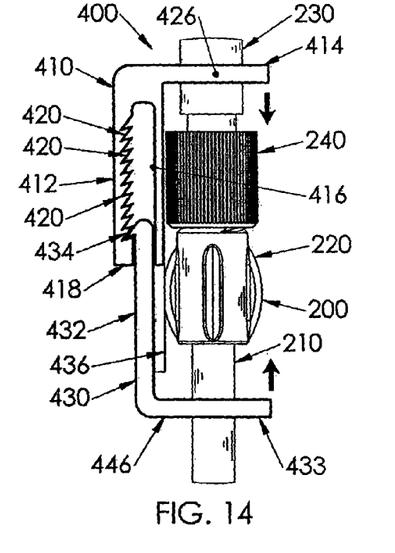
FIG. 14 is a side elevational view of the luer clip of FIG. 11, with a luer connection inserted therein prior to adjustment of the distance between the clip's two clamping portions.

Referring now to FIG. 14, the catheter assembly 200 is connected to the extracorporeal bloodline 230, with the female luer 220 of the catheter assembly 200 releasably connected to the male luer 240 of the extracorporeal bloodline 230.

Preferably, the extracorporeal bloodline 230 is inserted between the leg portions 422, 424 of the proximal portion 410 and into the generally U-shaped opening 426 such that the first leg 412 is disposed toward the distal portion 430. Similarly, the extension tube 210 is inserted between the leg portions 442, 444 of the distal portion 430 and into the generally U-shaped opening 446 such that the first leg 432 is disposed toward the proximal portion 410. The first leg 432 of the distal portion 430 is then inserted into the insertion slot 416 and the proximal portion 410 and the distal portion 430 are drawn toward each other, while securing the female luer 220 of the catheter assembly 200 and the male luer 240 of the extracorporeal bloodline 230 between the second leg 414 of the proximal portion 410 and the second leg 433 of the distal portion 430. The locking pawl 434 engages the ratchet teeth 420 so that the first leg 432 of the distal portion 430 can only be advanced in the proximal direction, securely retaining the distal portion 430 and the proximal portion 410 together. The clip 400 now securely connects the catheter assembly 200 and the extracorporeal bloodline 230.

To remove the clip 400, it is preferred that the clip 400 is snapped apart, so that the clip 400 may not be reused. In such an instance, it is preferred that the clip 400 is constructed from a relatively brittle material, such as ABS or other suitable material. Alternatively, the clip 400 may be removed by forcing the locking pawl 434 away from the ratchet teeth 420 and pulling the proximal portion 410 and the distal portion 430 away from each other. In such an instance, it is preferred that the clip 400 is constructed from polyethylene, polypropylene, or some other suitable material.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

The invention claimed is:

1. A clip for retaining a first flexible medical conduit to a second flexible medical conduit, wherein the first conduit includes a first connector and the second conduit includes a second connector releasably connected to the first connector, wherein the clip comprises:
   a proximal clip portion, a distal clip portion and a base portion adjustably connecting the proximal clip portion to the distal clip portion;
   wherein the proximal clip portion has a first proximal leg and a second proximal leg; wherein the second proximal leg is attachable to the first connector in a snap fit;
   wherein the distal clip portion has a first distal leg and a second distal leg;
   wherein the second distal leg is attachable to the second connector in a snap fit;
   wherein together the first proximal leg and the first distal leg define the base portion and the first distal leg is insertable into an insertion slot of the first proximal leg; and
   wherein a locking section is defined proximate an end of the first distal leg adapted to lock with one of a plurality of complementary locking elements arrayed along the insertion slot, and the first distal leg end is exposed by the first proximal leg to be accessed for unlocking from the one locking element, all such that the proximal and distal clip portions are adapted to be both adjustably and releasably connected without the necessity of additional components.

2. The clip according to claim 1, wherein the complementary locking elements comprise a plurality of locking slots.

3. The clip according to claim 2, wherein the first distal leg comprises a beveled tab disposed proximate the free end thereof adapted to mate with one of the plurality of locking slots of the first proximal leg, and the beveled tab is exposed by the first proximal leg to be accessed for delatching from the one locking slot.

4. The clip according to claim 1, wherein the complementary locking elements comprise a plurality of ratchet teeth extending therefrom.

5. The clip according to claim 4, wherein the first distal leg comprises a locking pawl disposed proximate the free end thereof adapted to mate with one of the plurality of ratchet teeth of the first proximal leg, and the locking pawl is exposed by the first proximal leg to be accessed for delatching from the one locking slot.

6. The clip according to claim 1, wherein the leg portions of the second proximal and distal legs include respective axially extending nubs to secure around ends of the first and second connectors adjacent thereto.

* * * * *